United States Patent
Margallo Balbás et al.

(10) Patent No.: US 9,869,541 B2
(45) Date of Patent: Jan. 16, 2018

(54) HIGH-SPEED OPTICAL COHERENCE TOMOGRAPHY USING MULTIPLE INTERFEROMETERS WITH SUPPRESSED MULTIPLE SCATTERING CROSS-TALK

(71) Applicant: MEDLUMICS S.L., Madrid (ES)

(72) Inventors: Eduardo Margallo Balbás, Madrid (ES); José Luis Rubio Guivernau, Madrid (ES)

(73) Assignee: Medlumics S.L., Madrid (ES)

( * ) Notice: Subject to any disclaimer, the term of this patent is extended or adjusted under 35 U.S.C. 154(b) by 0 days.

(21) Appl. No.: 15/213,293

(22) Filed: Jul. 18, 2016

(65) Prior Publication Data
US 2017/0023350 A1    Jan. 26, 2017

Related U.S. Application Data

(60) Provisional application No. 62/195,573, filed on Jul. 22, 2015.

(51) Int. Cl.
   *G01B 9/02* (2006.01)
   *A61B 5/00* (2006.01)
   *A61B 3/10* (2006.01)

(52) U.S. Cl.
   CPC .......... *G01B 9/0207* (2013.01); *A61B 5/0066* (2013.01); *G01B 9/02027* (2013.01);
   (Continued)

(58) Field of Classification Search
   CPC ............ G01B 9/02091; G01B 9/02015; G01B 9/02027; G01B 9/02028
   See application file for complete search history.

(56) References Cited

U.S. PATENT DOCUMENTS

2012/0044499 A1*  2/2012  Shimoyama ........... A61B 3/102
                                                  356/479
2012/0062901 A1*  3/2012  Yoshida ............... A61B 5/0066
                                                  356/479
(Continued)

FOREIGN PATENT DOCUMENTS

| JP | 2010 276462 A2 | 12/2010 |
| WO | WO 2010/134624 A1 | 11/2010 |
| WO | WO 2014/089504 A1 | 6/2014 |

OTHER PUBLICATIONS

Karamata, "Multiple Scattering in Wide-Field Optical Coherence Tomography," Thesis EPFL, 2004; 103 pages.
(Continued)

*Primary Examiner* — Jonathan Hansen
(74) *Attorney, Agent, or Firm* — Sterne, Kessler, Goldstein & Fox P.L.L.C.

(57) ABSTRACT

A system for optical coherence tomography using multiple interferometers presented. The interferometry system includes a source configured to generate a variable wavelength light beam. A first splitter is configured to split the variable wavelength light beam to at least a first light beam and a second light beam. A first delay element is configured to delay the first light beam by a first time delay. A second delay element is configured to delay the second light beam by a second time delay, such that the delayed first light beam and the delayed second light beam are out of coherence with each other. A first interferometer is configured to receive the delayed first light beam as an input. A second interferometer is configured to receive the delayed second light beam as an input.

43 Claims, 9 Drawing Sheets

(52) U.S. Cl.
CPC ..... *G01B 9/02056* (2013.01); *G01B 9/02075* (2013.01); *G01B 9/02091* (2013.01); *A61B 3/102* (2013.01)

(56) References Cited

U.S. PATENT DOCUMENTS

2013/0010262 A1\* 1/2013 Sato ..................... A61B 3/102
　　　　　　　　　　　　　　　　　　　　　351/206
2014/0118748 A1\* 5/2014 Rubio Guivernau A61B 5/0066
　　　　　　　　　　　　　　　　　　　　　356/479

OTHER PUBLICATIONS

Castillo et al., "Ten Channel Interferometer for Endoscopic Parallel Optical Coherence Tomography," Optical Society of America, 2005; 1 page.

\* cited by examiner

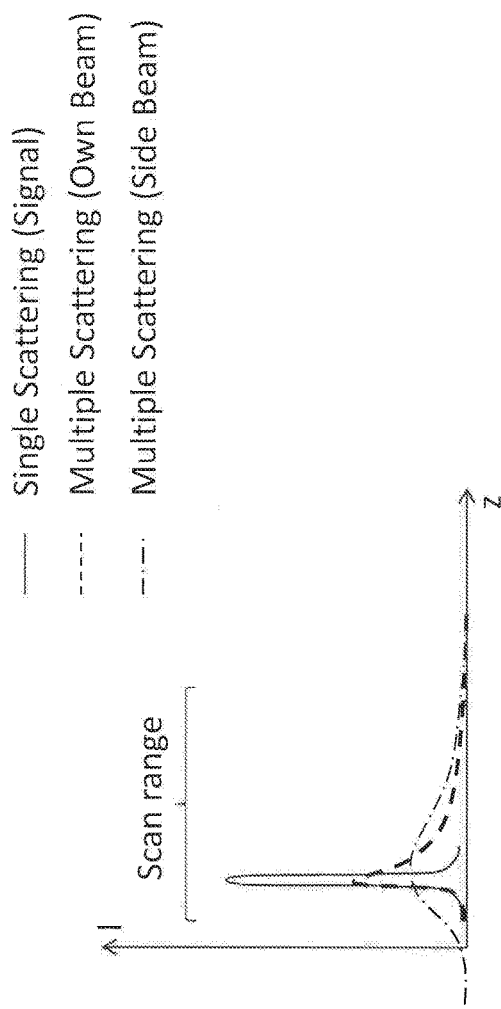
FIG. 9A.
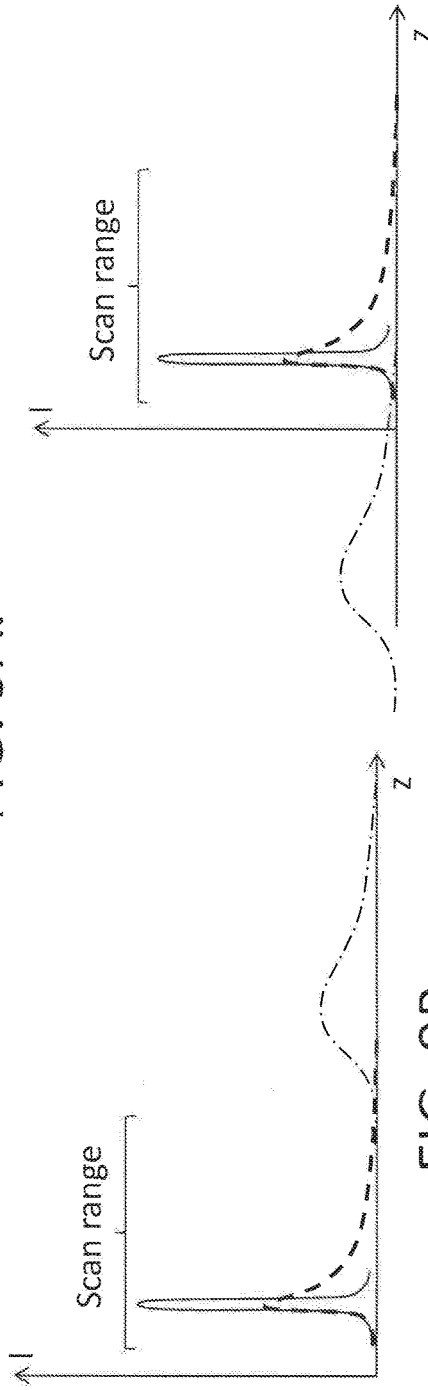
FIG. 9B.
FIG. 9C.

HIGH-SPEED OPTICAL COHERENCE TOMOGRAPHY USING MULTIPLE INTERFEROMETERS WITH SUPPRESSED MULTIPLE SCATTERING CROSS-TALK

This application claims priority to application Ser. No. 62/195,573 filed Jul. 22, 2015, which is hereby incorporated by reference in its entirety.

BACKGROUND

Field

Embodiments of the invention relate to the field of optical coherence tomography.

Background

Optical Coherence Tomography (OCT) is a technique for the generation of medical images that can provide axial information at a high resolution using a broadband light source and an interferometric detection system. It has found a wide range of uses, from cardiology to ophthalmology and gynecology, and for in-vitro sectional studies of biological materials.

Axial information is obtained in OCT through interferometric methods. One approach to generate images (2D) and volume representations (3D) of the histology of tissue is to move the beam laterally over the area of interest. This movement has been traditionally done by means of mechanical displacement of some optical element within the system, such as the waveguide in the case of fiber-based systems. Alternatively, the sample can be moved underneath a stationary beam. The most common solution utilizes a moving mirror in the beam path in the sample arm of the interferometer. Although this method is effective, it has drawbacks, especially in terms of reliability, manufacturing cost, maintenance cost, complexity of adjustment, final system size, etc. The use of MOEMS technology (Micro-opto-electro-mechanical systems) has been proposed and demonstrated for situations in which conventional mirrors are not acceptable, such as in catheters or laparoscopic instruments. However, these devices suffer from many of the same problems as their macroscopic versions and they pose their own challenges in terms of encapsulation, sterilization, etc.

One approach for providing a lateral scan over a sample is to use multiple beams. An example of this was proposed in WIPO Patent Application Publication WO 2010/134624. Several complete interferometers working in parallel are described that only share the light source. As such, the sample arm of every interferometer consists of a single optical path, leading to a structurally complicated system.

High-speed Optical Coherence Tomography (OCT) imaging is important for 3D scans of large tissue volumes, for the evaluation of fast dynamics in the sample and in indications prone to motion artifacts because of mechanical instability or body movements. Meeting this goal may require a significant increase in actual acquisition speed beyond the line speed of a single axial scanner (which is fixed by the physical properties of the external cavity or delay line) to obtain a sufficiently high sampling rate. Also, it may require improving the signal-to-noise (SNR) of the system to ensure good image quality in spite of high speeds. After optimization of system optics and electronics, and given usage of Swept Source OCT (SS-OCT) or Time Domain OCT (TD-OCT) implementations, this translates into increasing the maximum tolerable optical radiation limits through an extension of its optical Etendue.

Full-field OCT systems may meet these goals a priori because of their construction. However, they may suffer from cross-talk between adjacent channels and image quality problems. Full-field OCT (FF-OCT) systems also require 2D imaging sensors, which may limit them practically to wavelengths where such sensors are affordable and have sufficient resolutions (currently only <1 µm). Such sensors also limit image acquisition speed to the frame rate of the imager. Line-scan OCT limits the parallel acquisition to a single line and uses a scanning element to gain additional directions. Although cross-talk is better than in FF-OCT, image quality is still significantly worse than in standard OCT.

A solution described in WIPO Patent Application Publication WO 2014/089504 uses a spatially expanded source that is conformed into a plurality of separate beams by means of a mechanically actuated mask. The beams are then scanned over the surface of the tissue to be analyzed in order to produce the images. As long as the separation of these beams is large (the sampling is sparse), cross-talk can be effectively reduced. The problems with this approach are the loss in optical throughput when the source is masked, the need for a 2D imager (especially at longer wavelengths), and the trade-off between dense sampling and cross-talk.

Another approach described in Japanese Patent Application Publication JP 2010276462 uses an OCT system with multiple interferometers for a Time Domain configuration having 1 or 2 superluminescent diodes (SLEDS), but does not avoid multiple scattering cross-talk.

BRIEF SUMMARY

Systems and methods for performing high-speed OCT using multiple interferometers with suppressed multiple scattering cross-talk is presented.

According to an embodiment, an interferometry system may include a source configured to generate a variable wavelength light beam. A first splitter may be configured to split the variable wavelength light beam into at least a first light beam and a second light beam. A first delay element may be configured to delay the first light beam by a first time delay. A second delay element may be configured to delay the second light beam by a second time delay, such that the delayed first light beam and the delayed second light beam are out of coherence with each other. A first interferometer may be configured to receive the delayed first light beam as an input. A second interferometer may be configured to receive the delayed second light beam as an input.

According to another embodiment, an interferometry system may include a source configured to generate a light beam. A first splitter may be configured to split the light beam into a first light beam and a second light beam. A second splitter may be configured to split the first light beam into at least a third light beam and a fourth light beam. A first delay element may be configured to delay the third optical beam with a first time delay. A second delay element may be configured to delay the fourth optical beam with a second time delay, such that the delayed third light beam and the delayed fourth light beam are out of coherence with each other. A first interferometer may be configured to receive the delayed third light beam as an input. A second interferometer may be configured to receive the delayed fourth light beam as an input.

In an embodiment, a method may include generating a source light beam with a variable wavelength. The method may further include splitting the source light beam into at least a first light beam and a second light beam, delaying the first light beam with a first time delay, and delaying the second light beam with a second time delay, such that the delayed first light beam and the delayed second light beam are out of coherence with each other. The method may also include inputting the delayed first light beam to a first interferometer, and inputting the delayed second light beam to a second interferometer.

In another embodiment a method may include generating a source light beam, splitting the source light beam into a first light beam and a second light beam, and splitting the first light beam into at least a third light beam and a fourth light beam. The method may further include delaying the third light beam by a first time delay, and delaying the fourth light beam by a second time delay, such that the delayed third light beam and the delayed fourth light beam are out of coherence with each other. The method may also include inputting the delayed third light beam to a first interferometer and inputting the delayed fourth light beam into a second interferometer.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIGS. 9A, 9B, and 9C illustrate (quasi-) diffusive photon propagation from lateral beams in various optical systems.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Figure 1:
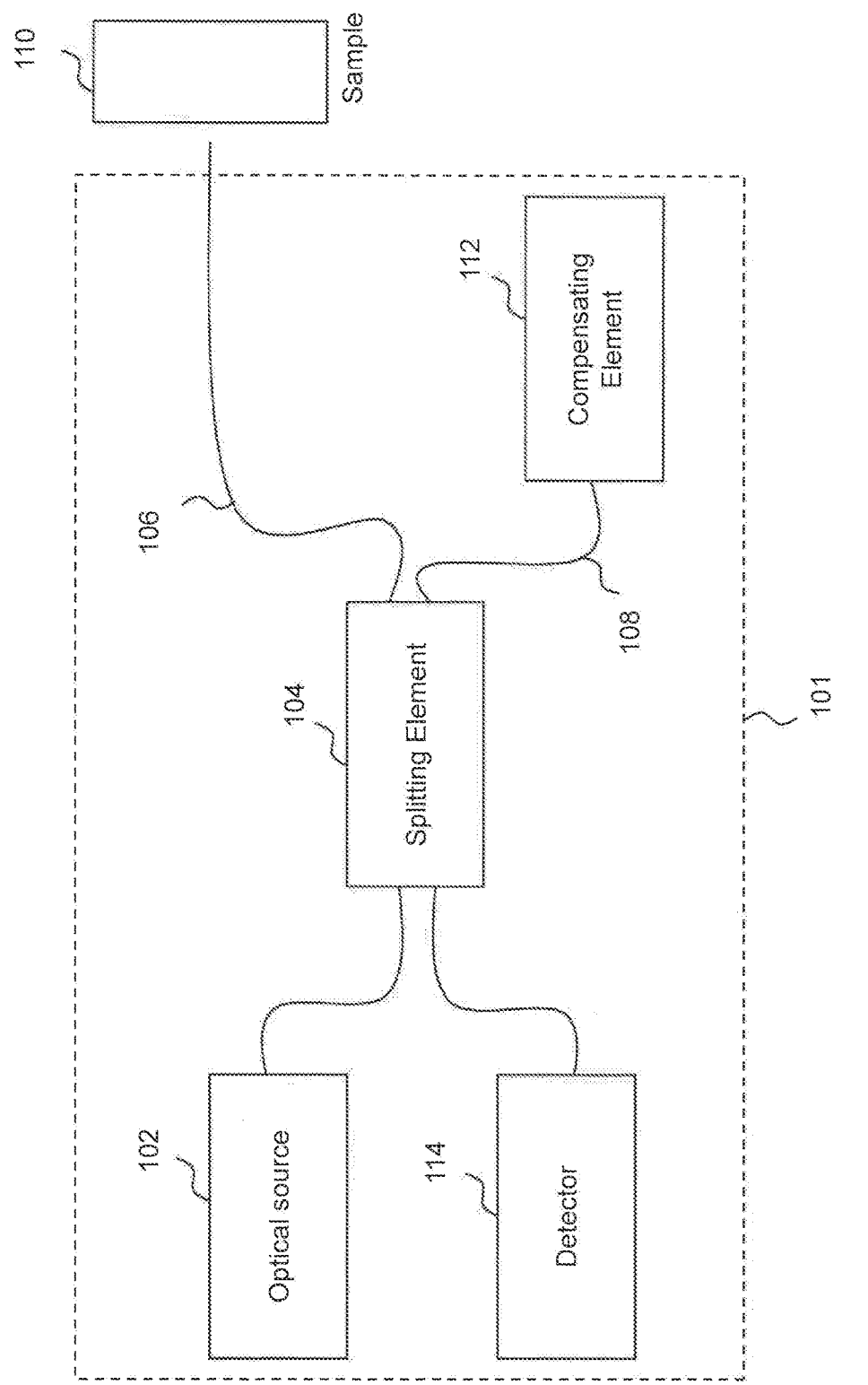
FIG. 1 is a block diagram of an OCT system, according to an embodiment.

FIG. 1 illustrates an OCT system 101, according to an embodiment. OCT system 101 includes a compensating element 112, and is used for imaging a sample 110. Compensating element 112 may be a variable delay system. For example, compensating element 112 may be used to provide a variable delay to the light within OCT system 101, while compensating for the effects of birefringence. The use of the term "light" may refer to any range of the electromagnetic spectrum. An example wavelength of light that may be used is infrared radiation at a wavelength of around 1.3 µm.

OCT system 101 further includes an optical source 102, a mixing splitter 104, a sample arm 106, a reference arm 108, and a detector 114. In an embodiment, detector 114 is a balanced detector pair.

In the embodiment shown, compensating element 112 is located within reference arm 108. However, it should be understood that compensating element 112 may also be located in sample arm 106. Alternatively, various components of compensating element 112 may be present in both sample arm 106 and reference arm 108. For example, components of compensating element 112 that introduce a variable delay to the light may be located in sample arm 106, while components that modulate different polarization modes of the light to reduce birefringence may be located in reference arm 108. In one example, sample arm 106 and reference arm 108 are optical waveguides, such as patterned waveguides or optical fibers. In an embodiment, all of the components of OCT system 101 are integrated onto a planar lightwave circuit (PLC). In another embodiment, at least all the components within compensating element 112 are integrated on the same substrate of a PLC. Other implementations may be considered as well, such as, for example, fiber optic systems, free-space optical systems, photonic crystal systems, etc.

It should be understood that OCT system 101 may include any number of other optical elements not shown for the sake of clarity. For example, OCT system 101 may include mirrors, lenses, gratings, splitters, micromechanical elements, etc., along the paths of sample arm 106 or reference arm 108.

Mixing splitter 104 is used to direct light received from optical source 102 to both sample arm 106 and reference arm 108. Mixing splitter 104 may be, for example, a bi-directional coupler, an optical splitter, or any other modulating optical device that converts a single beam of light into two or more beams of light.

Light that travels down sample arm 106 ultimately impinges upon sample 110. Sample 110 may be any suitable sample to be imaged, such as tissue. During an OCT procedure, the light scans at a certain depth within sample 110 and the scattered radiation is collected back into sample arm 106. In another embodiment, the scattered radiation is collected back into a different waveguide than the transmitting waveguide. The scan depth may be chosen via the delay imposed on the light within compensating element 112.

Light within sample arm 106 and reference arm 108 is recombined before being received at detector 114. In the embodiment shown, the light is recombined by mixing splitter 104. In another embodiment, the light is recombined at a different optical coupling element than mixing splitter 104.

For the sake of clarity, compensating element 112 is used to describe the components that introduce variable delay as well as reduce birefringence. Within compensating element 112, one may categorize the set of components related to introducing variable delay as a variable delay unit and the set of components related to reducing birefringence as an optical modulating unit.

Figure 6:
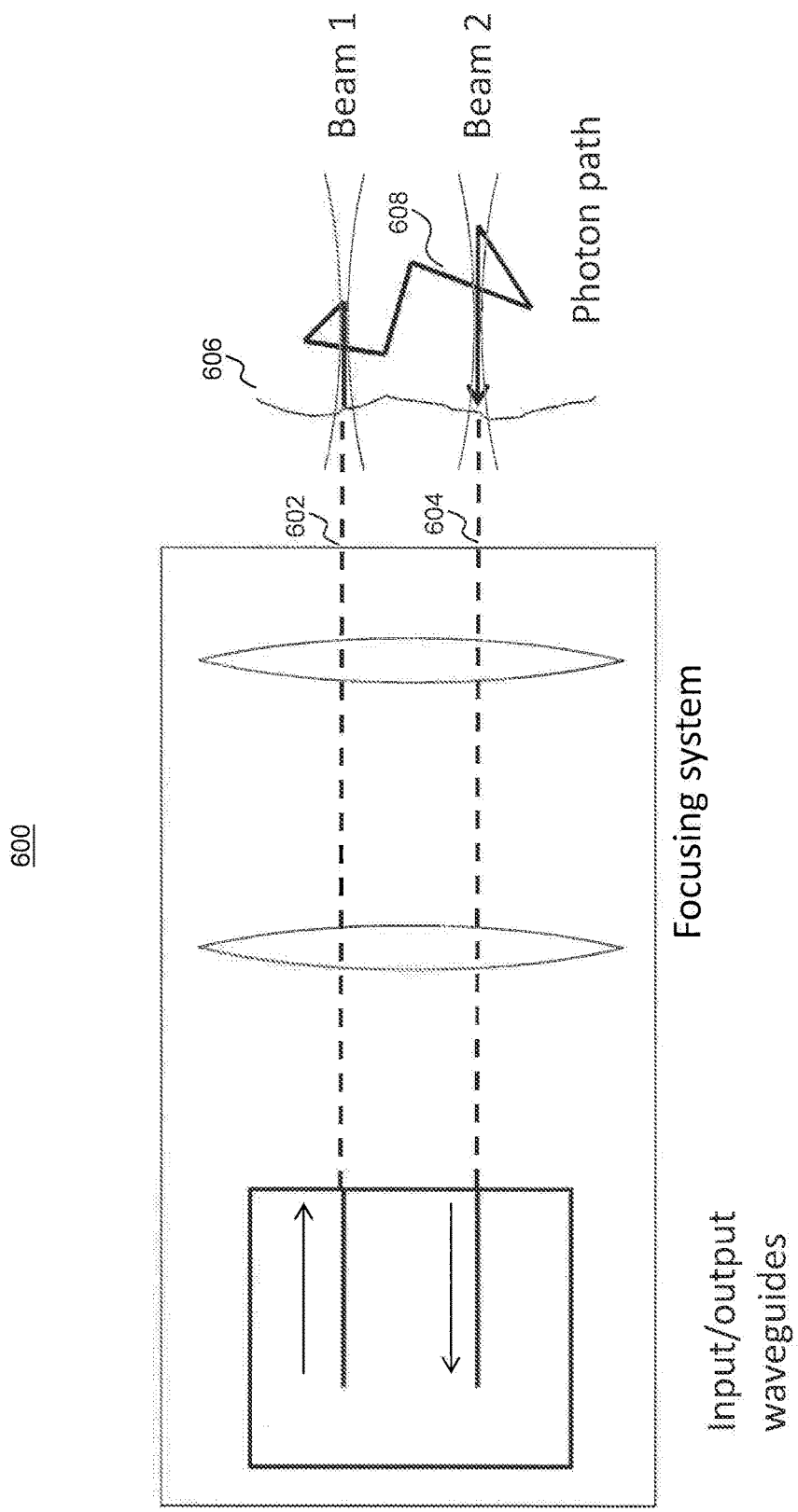
FIG. 6 illustrates an optical system focusing light from two output apertures on tissue.

High-speed OCT can be achieved by expanding the Etendue of the system through the use of multiple interferometers. Typically, adjacent interferometry signals may interfere due to cross-talk between channels caused by multiple scattering. Such interference may reduce image quality. Specifically, wide-angle multiple scattering causes crosstalk in OCT systems with more than one simultaneous optical aperture. FIG. 6 shows an example optical system 600 for focusing light from two output apertures 602 and 604 on tissue 606. FIG. 6 illustrates the multiple scattering effect, where a multiply scattered photon 608 (in a quasi-diffusive regime) coming from the excitation in a Beam 1 channel is collected by a Beam 2 channel and may contribute to the interference signal for Beam 2 channel.

In a typical tissue optics setting with strong anisotropy of scattering (for example, anisotropy factor g>0.8), wide-angle scattered photon intensity producing cross-talk between adjacent beams decreases more slowly with penetration depth than single-scattering. This is due to the longer characteristic distances of a diffusive or quasi-diffusive light propagation compared to the path length of single-scattering ballistic photons according to the Beer-Lambert law.

Figure 7:
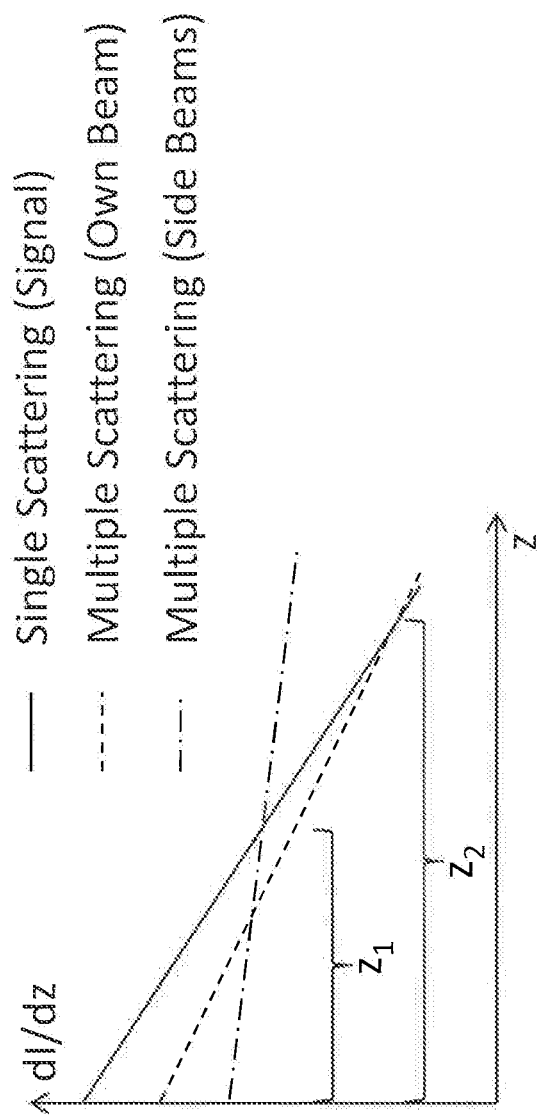
FIG. 7 illustrates maximum potential imaging depth in various optical systems.

Cross-talk between adjacent beams due to wide-angle scattered photon intensity also decreases more slowly than small-angle multiple scattering (in a non-diffusive regime) for excitation light coming from the same aperture that is used for collection. This reduces the actual maximum imaging depth compared to the single-scattering contribution. Imaging depth may be defined as the depth in the tissue where the contribution of single and multiple scattered photons to the OCT signal is equal. FIG. 7 illustrates this concept. As shown in FIG. 7, ignoring focus effects, the maximum potential imaging depth $z_2$ goes down to $z_1$ when multiple scattering cross-talk between apertures takes place.

Figure 8:
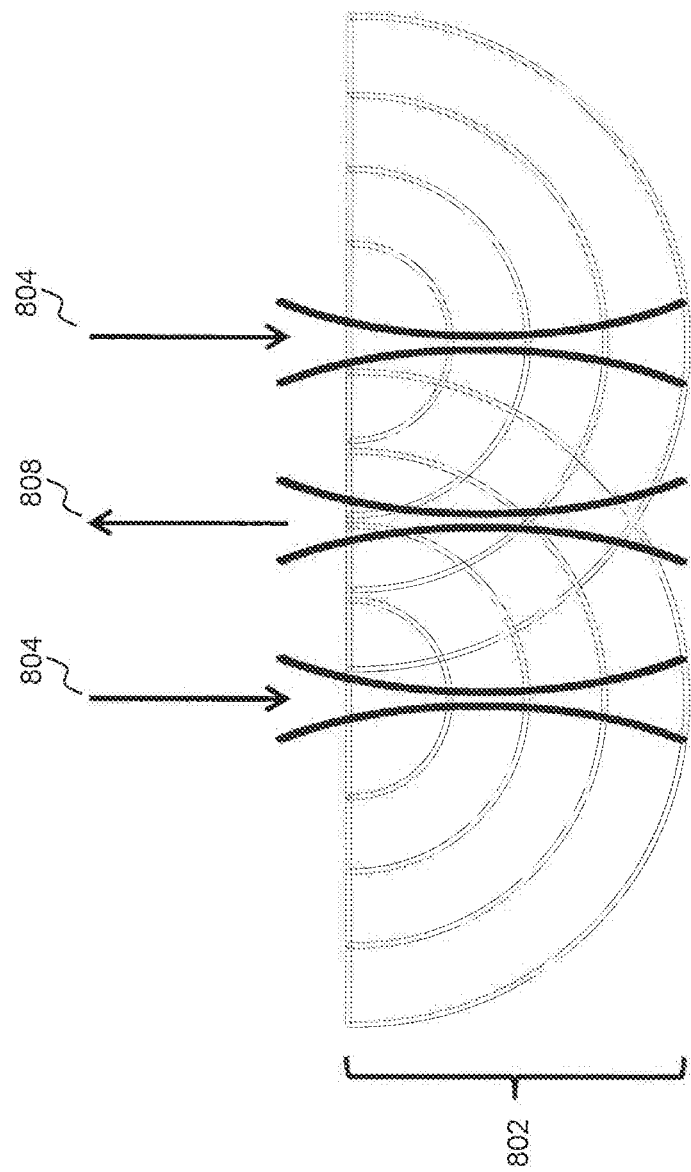
FIG. 8 illustrates multiply scattered photons generating cross-talk between simultaneously active channel beams.

This multiple scattering cross-talk effect is further illustrated in FIG. 8. In FIG. 8, diffusive or quasi-diffusive photon propagation from two lateral beams 804 contribute to the collected power in a middle beam 808. Constant fluence lines 802 correspond to the diffusive or quasi-diffusive fields generated by two independent excitation apertures. In FIG. 8, constant fluence lines 802 are overlaid on a representation of the corresponding excitation beams 804 and collection middle beam 808. The addition of multiple scattering contributions from excitation sources that are non-confocal with collection at distances shorter than the diffusion length for photon transport further reduce imaging depth and contrast.

FIGS. 9A, 9B, and 9C show the effect of the different multiple scattering contributions on the interference signal generated by a differential reflector at a fixed depth in tissue. The information-carrying single-scattering component has a width that is related to the coherence length of the source in a dispersion-adjusted OCT system. FIG. 9A shows an example intensity of photon propagation before adding a delay to shift the background interference due to multiple scattering out of coherence. FIG. 9B shows an example intensity of photon propagation after introducing a delay in an adjacent channel. FIG. 9C shows example reciprocal behavior of intensity of photon propagation in the delayed adjacent channel with respect to the excitation in the collection channel shown in FIG. 9B.

As shown in FIGS. 9A-9C, the small-angle multiple scattering caused by excitation with the same aperture as used for collection cannot be decoupled from the single-scattering contribution, and adds a tail to the collected signal that degrades contrast and ultimately limits system imaging depth. The multiple scattering contributions from adjacent apertures that are non-confocal with a collection aperture add a background interference with a larger path-length dispersion. Further discussion of such scattering may be found in B. Karamata, "Multiple Scattering in Wide-Field Optical Coherence Tomography," Thesis EPFL (2004), which is incorporated by reference herein in its entirety.

In embodiments of the invention described herein, cross-talk between adjacent channels in a multi-interferometer system is reduced by shifting the multiple scattering contributions from adjacent apertures out of coherence between each other. This allows for dense beam concentration in an imaging volume without compromising penetration depth and image contrast. Such shifting out of coherence may be achieved by adding a delay between the different active apertures, as described with respect to some embodiments herein. When such shifting occurs, the reciprocal behavior between excitation and collection beams should be taken into account. This is because the intensity of photon propagation of the multiple-scattering background (as shown in FIGS. 9A-9C) is non-symmetrical and is advanced (and not delayed) relative to multiple scattering contributions from adjacent apertures. Therefore, as the multiple scattering contribution is in general non-symmetrical with respect to path-length, the tail decaying at slowest rate may be used to compute the required relative delay between channels.

Some embodiments herein unlink image speed enhancement from image degradation due to the cross-talk caused by multiple scattering. By suppressing this cross-talk, which may be caused by the presence of multiple scattering, embodiments keep the advantages of increased speed and potential SNR and regain optimum image quality.

An embodiment includes an OCT system that generates a plurality of separate scanning interferometers from a single tunable device, while ensuring that cross-talk between them because of multiple scattering is kept to a minimum. Embodiments include and may be applied to swept source (SS) or time domain (TD) systems.

Using multiple interferometers may multiply the effective line rate by the number of replicated interferometers. In some embodiments described herein, cross-talk between channels is suppressed by means of multiplexing, such as frequency multiplexing or time multiplexing between channels. Some embodiments provide shifting adjacent interferometer signals out of coherence with respect to each other, such that any significant multiple scattering contributions from beams/apertures are out of coherence with respect to each other. In embodiments, time delays provide such shifting. For example, the appropriate time delays may be determined by taking into account the non-symmetrical property of multiple scattering caused by excitation by the beam from the same aperture that is also used for collection. These relative time delays may depend on the geometrical configuration of the different beams and on sample properties, and can be determined experimentally or through simulation tools (like Monte Carlo methods).

Figure 2:
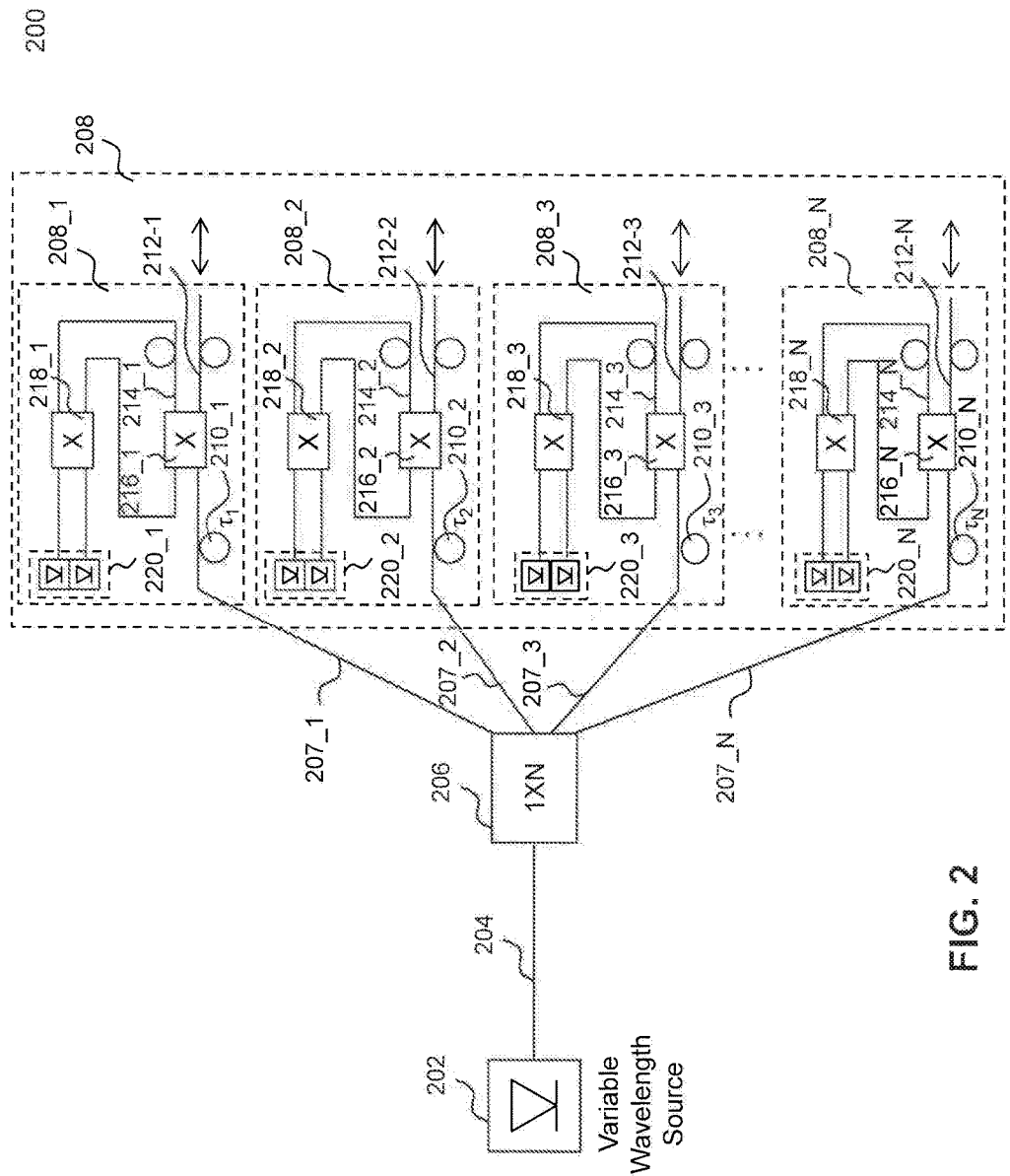
FIG. 2 is a block diagram of a Swept Source OCT system, according to an embodiment.

FIG. 2 illustrates a block diagram of a multi-interferometer Swept Source OCT system 200, according to an embodiment. OCT system 200 includes a variable wavelength optical source 202, a splitter 206, and interferometers 208.

A path 204 connects variable wavelength source 202 to splitter 206. Beam path 204 may be a waveguide, according to an embodiment. Splitter 206 may split beam of radiation generated by variable wavelength source 202 into multiple beams over paths 207_1, 207_2, 207_3, . . . , 207_N. Splitting element 206 may be, for example, a bi-directional coupler, an optical splitter, or any other optical device that converts a single beam of light into two or more beams of light.

According to an embodiment, each output of splitter 206 is received by an interferometer of interferometers 208. Each output of splitter 206 may have the same functionality as an optical source, for example optical source 102, for its corresponding interferometer. For example a first output of splitter 206, on path 207_1, is received by interferometer 208_1. A second output of splitter 206, on path 207_2, is received by interferometer 208_2. A third output of splitter 206, on path 207_3, is received by interferometer 208_3. An $N^{th}$ output of splitter 206, on path 207_N, is received by interferometer 208_N, wherein N is an integer.

According to an embodiment, each output beam of splitter 206 is delayed using a delay element. For example, the beam over path 207_1 may be delayed by time delay $\tau_1$ using delay element 210_1, the beam over path 207_2 may be delayed by time delay $\tau_2$ using delay element 210_2, the beam over path 207_3 may be delayed by time delay $\tau_3$ using delay element 210_3, and the beam over path 207_N may be delayed by time delay $\tau_N$ using delay element 210_N.

According to an embodiment, delay elements 210_1, 210_2, 210_3, and 210_N may be implemented as part of their corresponding interferometers. In another embodiment, delay elements 210_1, 210_2, 210_3, and 210_N may be implemented on their respective beam paths outside their corresponding interferometers.

The example embodiment of FIG. 1 may be incorporated into a multiple-interferometer 208 construction for SS-OCT with separation of beams on paths 207_1, 207_2, 207_3, . . . , 207_N by means of coherence shifting created by different delays $\tau_1, \tau_2, \tau_3, \ldots, \tau_N$, respectively. The time differences between the optical signals delayed according to delays $\tau_1, \tau_2, \tau_3, \ldots, \tau_N$, may be larger than the coherence time of the source increased by a factor of the reduced mean free path of light in a tissue undergoing tomography at the working wavelength, depending on the conditions of multiple scattering.

In embodiments, differences between any pair of delays $\tau_1, \tau_2, \tau_3, \ldots, \tau_N$, are large enough to shift adjacent interferometer signals out of coherence with respect to each other, as described above. For example, time delay $\tau_i$, wherein 1≤i≤N, may be determined by taking into account the non-symmetrical shape of multiple scattering caused by and detected by interferometer 208_i. For example, the difference between a first time delay applied to a first beam and a second time delay applied to a second beam may be greater than a coherence time of the first and second beams.

In an embodiment, outputs 207 of splitter 206, after being delayed by delay elements 210, are fed to mixing splitters 216 in each respective interferometer. Mixing splitter 216 then generate sample signals on sample arms 212, and reference signals on reference arms 214. For example mixing splitter 216_1 generates a sample signal on arm 212_1 of interferometer 208_1, and a reference signal on arm 214_1 of interferometer 208_1.

The reference signal, and sample signal after being scattered by a tissue undergoing tomography, are fed to mixing splitters 218 that are connected to detecting elements 220 in each interferometer. Detecting elements 220 each may include two detectors in a balanced configuration. The lengths of each individual sample and reference arm pair may determine actual interference within each channel. The length of the arms may be equal for all replicas and can be tuned to maximize image quality. Delay elements on the sample and reference arms may be used for tuning.

Figure 3:
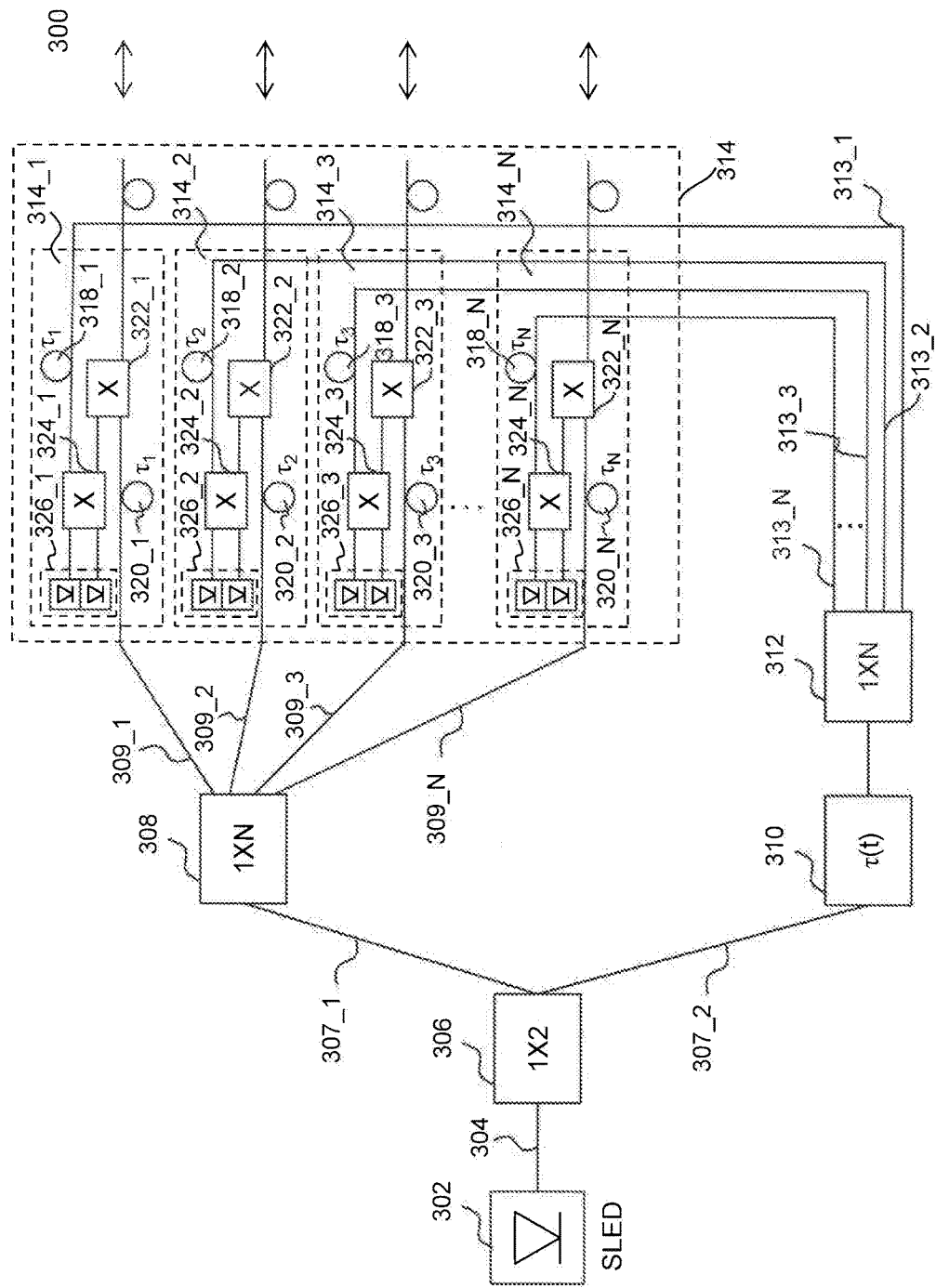
FIG. 3 is a block diagram of a Time Domain OCT system, according to an embodiment

FIG. 3 illustrates a block diagram of a Time Domain OCT system 300, according to an embodiment. OCT system 300 may include a source 302, a first splitter 306, a second splitter 308, a variable delay element 310, a third splitter 312, and interferometers 314.

Source 302 generates a beam of radiation. In an embodiment, source 302 is a superluminescent diode (SLED). A path 304 may connect source 302 to splitter 306. Beam path 304 may be a waveguide, according to an embodiment. Splitter 306 may split the beam of radiation generated by source 302 into two beams over paths 307_1 and 3072. Splitting element 306 may be, for example, a bi-directional coupler, an optical splitter, or any other modulating optical device that converts a single beam of light into two or more beams of light.

According to an embodiment, the output of splitter 306 over path 307_1 is received by splitter 308, and the output of splitter 306 over path 307_2 is received by variable delay element 310.

In an embodiment, the beam on path 307_1 is used to generate a sample beam for interferometry and the beam on path 307_2 is used to generate a reference beam for interferometry. Splitting the sample and reference signal in this manner may prevent the need for a delay line in each individual interferometer.

In an embodiment, variable delay element 310 provides a common variable delay to the beam on path 307_2. Variable delay element 310 may provide group delay modulation. The output of variable delay element 310 may be split, using splitter 312, into output beams on output paths 313. Splitting element 312 may be, for example, a bi-directional coupler, an optical splitter, or any other modulating optical device that converts a single beam of light into two or more beams of light.

Each beam on paths 313 may be received by respective interferometers 314. For example a first output of splitter 312, on path 313_1, may be received by interferometer 314_1. A second output of splitter 312, on path 313_2, may be received by interferometer 314_2. A third output of splitter 312, on path 313_3, may be received by interferometer 314_3. An $N^{th}$ output of splitter 312, on path 313_N, may be received by interferometer 314_N, where N is an integer.

In an embodiment, splitter 308 splits the beam on path 307_1 into output beams on paths 309. Each beam on paths 309 may be received by respective interferometers 314. For example, a first output of splitter 308, on path 309_1, may be received by interferometer 314_1. A second output of splitter 308, on path 3092, may be received by interferometer 314_2. A third output of splitter 308, on path 309_3, may be received by interferometer 314_3. An $N^{th}$ output of splitter 308, on path 309_N, may be received by interferometer 314_N, where N is an integer.

According to an embodiment, each output beam of splitter 312 is delayed using a delay element. For example, the beam over path 313_1 may be delayed by time delay $\tau_1$ using delay element 318_1, the beam over path 313_2 may be delayed by time delay $\tau_2$ using delay element 318_2, the beam over path 313_3 may be delayed by time delay $\tau_3$ using delay element 318_3, and the beam over path 313_N may be delayed by time delay $\tau_N$ using delay element 318_N.

According to an embodiment, each output beam of splitter 308 is delayed using a delay element 320. For example, the beam over path 309_1 may be delayed by time delay $\tau_1$ using delay element 320_1, the beam over path 309_2 may be delayed by time delay $\tau_2$ using delay element 320_2, the beam over path 309_3 may be delayed by time delay $\tau_3$ using delay element 320_3, and the beam over path 309_N may be delayed by time delay $\tau_N$ using delay element 320_N.

In an embodiment, the same delays may be applied to beams on paths 309 and the beam on a path 313 corresponding to a same interferometer. For example, the delay introduced by delay element 318_1 on a beam on path 313_1 may be the same as the delay introduced by delay element 320_1 on a beam on path 309_1.

In embodiments, differences between any pair of delays $\tau_1, \tau_2, \tau_3, \ldots, \tau_N$ are large enough so as to preclude any significant cross-talk between channels. The time differences between the optical signals delayed according to delays $\tau_1, \tau_2, \tau_3, \ldots, \tau_N$, may be larger than the coherence time of the source increased by a factor of the reduced mean free path of light in a tissue undergoing tomography at the working wavelength, depending on the conditions of multiple scattering.

In embodiments, differences between any pair of delays $\tau_1, \tau_2, \tau_3, \ldots, \tau_N$, are large enough to shift adjacent interferometer signals out of coherence with respect to each other, as described above. For example, time delay $\tau_i$, wherein 1≤i≤N, is determined by taking into account the non-symmetrical shape of multiple scattering caused by and detected by interferometer 208_i. For example, the difference between a first time delay applied to a first beam and a second time delay applied to a second beam may be greater than a coherence time of the first and second beams.

According to an embodiment, delay elements 318 and 320 may be implemented as part of their corresponding interferometers. In another embodiment, delay elements 318 and 320 may be implemented on their respective beam paths outside their corresponding interferometers.

In an embodiment, beams on each path 309, after being delayed by delaying elements 320, are fed to respective output mixing splitters 322. Mixing splitters 322 send the light to the sample and direct reflections coming back from the sample to a first input of respective mixing splitters 324. For example, the beam on path 309_1, after being delayed by delaying element 320_1, is fed to output mixing splitters 322_1 to generate a sample light from interferometer 314_1. The reflection of the sample light is then fed to a first input of mixing splitter 324_1.

Matched reference lines 313, after being delayed by delaying elements 318, are fed to respective second inputs of mixing splitters 324, whose outputs are in turn connected to respective detecting elements 326 in each interferometer 314. Detecting elements 326 each may include two detectors in a balanced configuration. For example, the beam on path 313_1, after being delayed by delaying element 318_1, is fed to a second input of mixing splitter 324_1 whose outputs are in turn connected to detecting elements 326_1.

If necessary, source 302 power may be amplified through an optical amplifier (e.g. an SOA or a doped fiber amplifier) so as to profit from the extended maximum allowable power manageable by the combination of interferometers.

Figure 4:
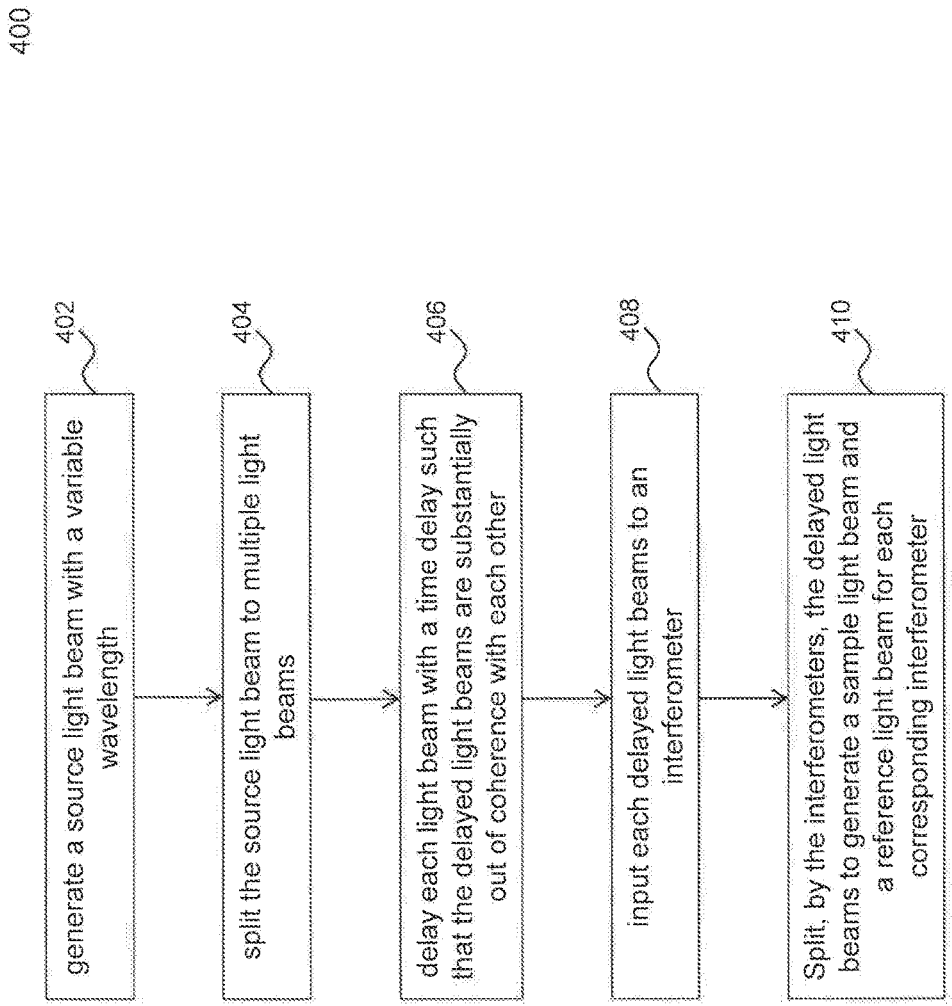
FIG. 4 is a flowchart of an example method, according to an embodiment.

FIG. 4 illustrates a flowchart of an example method 400, according to an embodiment. At step 402, a source light beam is generated with a variable wavelength. At step 404, the source light beam is split into multiple light beams. At step 406, each light beam is delayed with a time delay such that any significant multiple scattering contributions from the delayed light beams are out of coherence with respect to each other, as described above.

At step 408, each delayed light beam is input to an interferometer.

At step 410, the interferometers split the respective delayed light beams to generate a sample light beam and a reference light beam for each corresponding interferometer.

As the result of such a method, scan time across the sample is decreased while optimum image quality is maintained, due to the simultaneous presence of multiple sample light beams where the effects of cross-talk due to multiple scattering are minimized by the lack of coherence between the beams.

Figure 5:
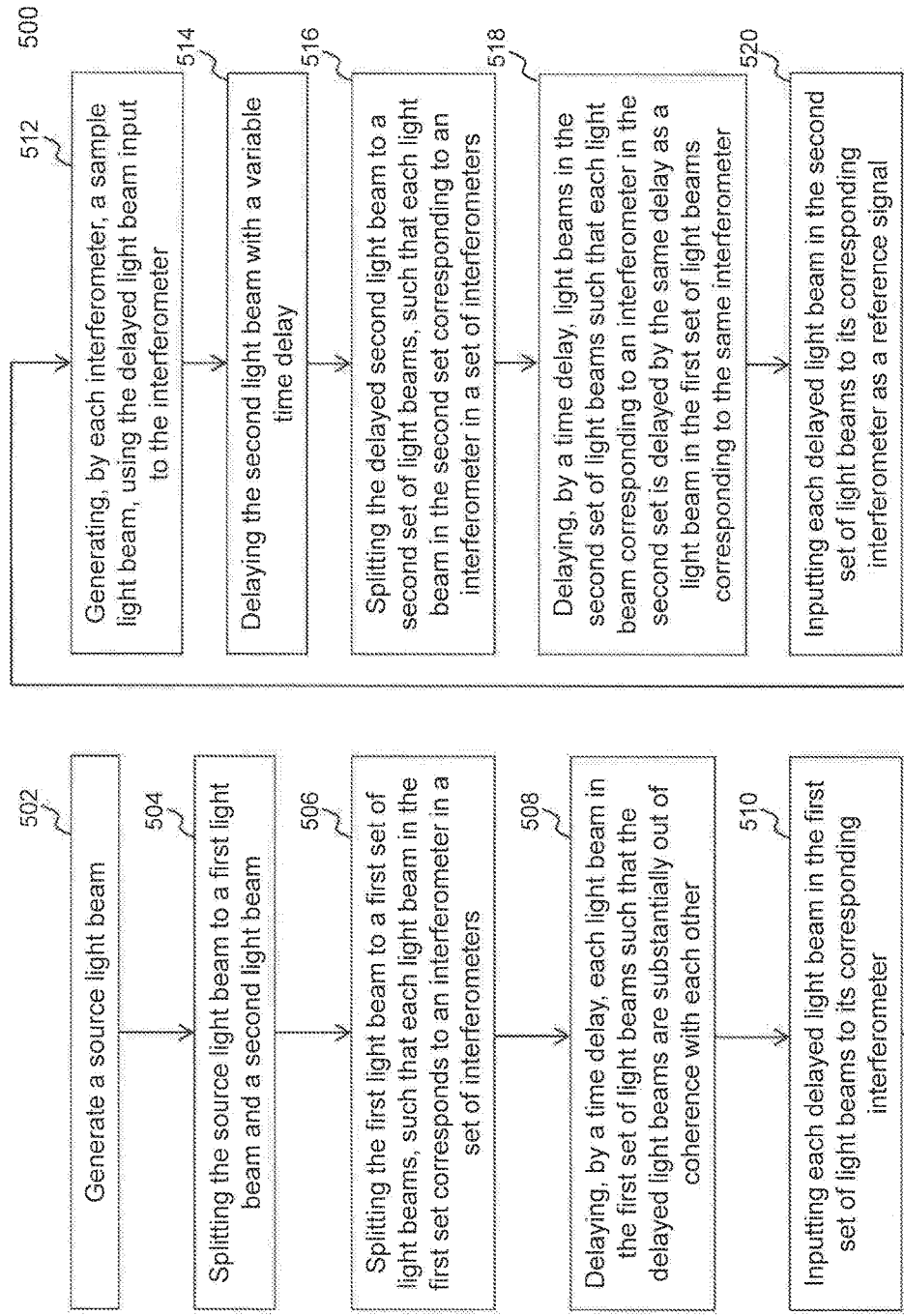
FIG. 5 is a flowchart of an example method, according to an embodiment.

FIG. 5 illustrates a flowchart of an example method 500, according to an embodiment. At step 502, a source light beam is generated. At step 504, the source light beam is split into a first light beam and a second light beam. At step 506, the first light beam is split into a first set of light beams, such that each light beam in the first set corresponds to a respective interferometer in a set of interferometers.

At step 508, each light beam in the first set of light beams is delayed, by a time delay, such that any significant multiple scattering contributions from the delayed light beams are out of coherence with respect to each other, as described above. At step 510, each delayed light beam in the first set of light beams is input to its corresponding interferometer. At step 512, each interferometer generates a sample light beam, using the delayed light beam input to the interferometer.

At step 514, the second light beam is delayed with a variable time delay. At step 516, the delayed second light beam is split into a second set of light beams, each light beam in the second set corresponding to an interferometer in a set of interferometers.

At step 518, light beams in the second set of light beams are delayed, by a time delay, such that each light beam corresponding to an interferometer in the second set is delayed by the same time delay as a light beam corresponding to the same interferometer in the first set of light beams. At step 520, each delayed light beam in the second set of light beams is input to its corresponding interferometer as a reference signal.

Again, as the result of such a method, scan time across the sample is decreased while optimum image quality is maintained, due to the simultaneous presence of multiple sample light beams where the effects of cross-talk due to multiple scattering are minimized by the lack of coherence between the beams.

Other embodiments may include free-space optics OCT implementations (Full Field) using modulation of group delay or phase applied through a spatial dense 2D modulator. In embodiments, wave guide paths may be replaced by optical beam sections.

Other embodiments may include fully separate OCT systems working together on a same sample and dividing the sample volume to be scanned between them. In embodiments, the sources are incoherent between each other and optical signals from two systems may not produce interference with each other in a way that contributes to the electrical signal band. In swept-source systems, instantaneous wavelengths may not follow exactly the same scan function, or optical delays between the sources may exceed coherence lengths.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An interferometry system comprising:
   a source configured to generate a variable wavelength beam of radiation;
   a first splitter configured to split the variable wavelength beam of radiation into at least a first beam of radiation and a second beam of radiation;
   a first delay element configured to delay the first beam of radiation by a first time delay;
   a second delay element configured to delay the second beam of radiation by a second time delay, such that the delayed first beam of radiation and the delayed second beam of radiation are out of coherence with respect to each other;
   a first interferometer configured to receive the delayed first beam of radiation as an input; and
   a second interferometer configured to receive the delayed second beam of radiation as an input.

2. The interferometry system of claim 1, wherein a difference between the first time delay and the second time delay is large enough to account for a non-symmetrical property of multiple scattering caused by the first beam of radiation.

3. The interferometry system of claim 1, wherein the first interferometer comprises a second splitter configured to split the delayed first beam of radiation to generate a first sample beam of radiation and a first reference beam of radiation.

4. The interferometry system of claim 3, wherein the first sample beam of radiation is an optical coherence tomography beam of radiation.

5. The interferometry system of claim 3, wherein the second interferometer comprises a third splitter configured to split the delayed second beam of radiation to generate a second sample beam of radiation and a second reference beam of radiation.

6. The interferometry system of claim 5, wherein the second sample beam of radiation is an optical coherence tomography beam of radiation.

7. The interferometry system of claim 1, wherein the first splitter is further configured to split the variable wavelength beam of radiation to generate a third beam of radiation.

8. The interferometry system of claim 7, further comprising:
   a third delay element configured to delay the third beam of radiation by a third time delay, such that the delayed third beam of radiation is out of coherence with respect to the delayed first beam of radiation and with respect to the delayed second beam of radiation; and
   a third interferometer configured to receive the delayed third beam of radiation as an input.

9. The interferometry system of claim 8, wherein the third interferometer comprises a second splitter configured to split the delayed third beam of radiation into a first sample beam of radiation and a first reference beam of radiation.

10. The interferometry system of claim 8, wherein differences between the third time delay and the first time delay and between the third time delay and the second time delay are large enough to account for non-symmetrical properties of multiple scattering caused by the delayed first beam of radiation and the delayed second beam of radiation, respectively.

11. The interferometry system of claim 1, wherein the first time delay is zero.

12. An interferometry system comprising:
   a source configured to generate a beam of radiation;
   a first splitter configured to split the beam of radiation into a first beam of radiation and a second beam of radiation;
   a second splitter configured to split the first beam of radiation into at least a third beam of radiation and a fourth beam of radiation;
   a first delay element configured to delay the third beam of radiation with a first time delay;
   a second delay element configured to delay the fourth beam of radiation with a second time delay, such that the delayed third beam of radiation and the delayed fourth beam of radiation are out of coherence with respect to each other;
   a first interferometer configured to receive the delayed third beam of radiation as an input; and
   a second interferometer configured to receive the delayed fourth beam of radiation as an input.

13. The interferometry system of claim 12, wherein a difference between the first time delay and the second time delay is large enough to account for a non-symmetrical property of multiple scattering caused by the third beam of radiation.

14. The interferometry system of claim 13, wherein the first interferometer comprises a mixing splitter configured to receive the delayed third beam of radiation and generate a first sample beam of radiation.

15. The interferometry system of claim 14, wherein the first sample beam of radiation is an optical coherence tomography beam of radiation.

16. The interferometry system of claim 12, wherein the second interferometer comprises a mixing splitter configured to receive the delayed fourth beam of radiation and generate a first sample beam of radiation.

17. The interferometry system of claim 16, wherein the first sample beam of radiation is an optical coherence tomography beam of radiation.

18. The interferometry system of claim 16, further comprising:
a variable delay element configured to delay the second beam of radiation by a variable delay;
a third splitter configured to split the delayed second beam of radiation into at least a fifth beam of radiation and a sixth beam of radiation;
a third delay element configured to delay the fifth beam of radiation by the first time delay; and
a fourth delay element configured to delay the sixth beam of radiation by the second time delay.

19. The interferometry system of claim 18, wherein the first interferometer is further configured to receive the delayed fifth beam of radiation as a reference input.

20. The interferometry system of claim 18, wherein the second interferometer is further configured to receive the delayed sixth beam of radiation as a reference input.

21. The interferometry system of claim 12, wherein the second splitter is further configured to split the first beam of radiation into a seventh beam of radiation.

22. The interferometry system of claim 21, further comprising:
a fifth delay element configured to delay the seventh beam of radiation with a third time delay such that the delayed seventh beam of radiation is out of coherence with the delayed third beam of radiation and the delayed fourth beam of radiation; and
a third interferometer configured to receive the delayed seventh beam of radiation as an input.

23. The interferometry system of claim 22, wherein differences between the third time delay and the first time delay and between the third time delay and the second time delay are large enough to account for non-symmetrical properties of multiple scattering caused by the delayed third beam of radiation and the delayed fourth beam of radiation, respectively.

24. The interferometry system of claim 22, wherein the third interferometer comprises a mixing splitter configured to receive the delayed seventh beam of radiation and generate a first sample beam of radiation.

25. The interferometry system of claim 24, wherein the third splitter is further configured to split the delayed second beam of radiation into an eighth beam of radiation.

26. The interferometry system of claim 25, further comprising:
a sixth delay element configured to delay the eighth beam of radiation with the third time delay.

27. The interferometry system of claim 26, wherein the third interferometer is further configured to receive the delayed eighth beam of radiation as a reference input.

28. The interferometry system of claim 12, wherein the first time delay is zero.

29. A method comprising:
generating a source beam of radiation with a variable wavelength;
splitting the source beam of radiation into at least a first beam of radiation and a second beam of radiation;
delaying the first beam of radiation with a first time delay;
delaying the second beam of radiation with a second time delay, such that the delayed first beam of radiation and the delayed second beam of radiation are out of coherence with each other;
inputting the delayed first beam of radiation to a first interferometer; and
inputting the delayed second beam of radiation to a second interferometer.

30. The method of claim 29, wherein a difference between the first time delay and the second time delay is large enough to account for a non-symmetrical property of multiple scattering caused by the first beam of radiation.

31. The method of claim 29, further comprising:
splitting, by the first interferometer, the delayed first beam of radiation to generate a first sample beam of radiation and a first reference beam of radiation; and
splitting, by the second interferometer, the delayed second beam of radiation to generate a second sample beam of radiation and a second reference beam of radiation.

32. The method of claim 31, wherein the first and second sample beams of radiation are optical coherence tomography beams of radiation.

33. The method of claim 31, further comprising:
splitting the source beam of radiation further into a third beam of radiation;
delaying the third beam of radiation with a third time delay, such that the delayed third beam of radiation is out of coherence with respect to the delayed first beam of radiation and with respect to the delayed second beam of radiation;
inputting the delayed third beam of radiation to a third interferometer; and
splitting, by the third interferometer, the delayed third beam of radiation to generate a third sample beam of radiation and a third reference beam of radiation.

34. The method of claim 33, wherein differences between the third time delay and the first time delay and the third time delay and the second time delay are large enough to account for non-symmetrical properties of multiple scattering caused by the delayed first beam of radiation and the delayed second beam of radiation, respectively.

35. The method of claim 29, wherein the first time delay is zero.

36. A method comprising:
generating a source beam of radiation;
splitting the source beam of radiation into a first beam of radiation and a second beam of radiation;
splitting the first beam of radiation into at least a third beam of radiation and a fourth beam of radiation;
delaying the third beam of radiation by a first time delay;
delaying the fourth beam of radiation by a second time delay, such that the delayed third beam of radiation and the delayed fourth beam of radiation are out of coherence with respect to each other;
inputting the delayed third beam of radiation to a first interferometer; and
inputting the delayed fourth beam of radiation to a second interferometer.

37. The method of claim 36, wherein a difference between the first time delay and the second time delay is large enough to account for a non-symmetrical property of multiple scattering caused by the third beam of radiation.

38. The method of claim 36, further comprising:
generating, by the first interferometer, a first sample beam of radiation, using the delayed third beam of radiation; and
generating, by the second interferometer, a second sample beam of radiation, using the delayed fourth beam of radiation.

39. The method of claim 38, wherein the first and second sample beams of radiation are optical coherence tomography beams of radiation.

40. The method of claim 36, further comprising:
delaying the second beam of radiation with a variable time delay;

splitting the delayed second beam of radiation into at least a fifth beam of radiation and a sixth beam of radiation;

delaying the fifth beam of radiation by the first time delay;

inputting the delayed fifth beam of radiation to the first interferometer as a first reference beam of radiation;

delaying the sixth beam of radiation by the second time delay; and inputting the delayed sixth beam of radiation to the second interferometer as a second reference beam of radiation.

41. The method of claim 40, further comprising:

splitting the first beam of radiation further into a seventh beam of radiation;

delaying the seventh beam of radiation by a third time delay, such that the delayed seventh beam of radiation is out of coherence with respect to the delayed third beam of radiation and with respect to the delayed fourth beam of radiation;

inputting the delayed seventh beam of radiation to a third interferometer; and generating, by the third interferometer, a first sample beam of radiation, using the delayed seventh beam of radiation.

42. The method of claim 41, wherein differences between the third time delay and the first time delay and the third time delay and the second time delay are large enough to account for non-symmetrical properties of multiple scattering caused by the third beam of radiation and the fourth beam of radiation, respectively.

43. The method of claim 41, further comprising:

splitting the delayed second beam of radiation further into an eighth beam of radiation;

delaying the eighth beam of radiation by the third time delay, such that the delayed eighth beam of radiation is out of coherence with respect to the delayed fifth beam of radiation and the delayed sixth beam of radiation; and inputting the delayed eighth beam of radiation to the third interferometer as a third reference beam of radiation.

\* \* \* \* \*